United States Patent [19]

Sanderson et al.

[11] Patent Number: 4,691,035

[45] Date of Patent: Sep. 1, 1987

[54] PURIFICATION OF PROPYLENE OXIDE BY TREATMENT WITH A SELECTED BASE AND INERT SALT

[75] Inventors: John R. Sanderson; Edward T. Marquis; William A. Smith, all of Austin; Kenneth P. Keating, Georgetown, all of Tex.

[73] Assignee: Texaco Inc., White Plains, N.Y.

[21] Appl. No.: 851,846

[22] Filed: Apr. 14, 1986

[51] Int. Cl.[4] ............................ C07D 301/32
[52] U.S. Cl. .................................. 549/542
[58] Field of Search ........................ 549/542

[56] References Cited

U.S. PATENT DOCUMENTS

| | | | |
|---|---|---|---|
| 2,550,847 | 5/1951 | Mitchell et al. | 549/542 |
| 2,622,060 | 12/1952 | Robeson et al. | 549/542 |
| 3,350,417 | 10/1967 | Binning et al. | 549/532 |
| 3,477,919 | 11/1969 | Lichtenwalter et al. | 549/542 |
| 3,838,020 | 9/1974 | Kageyama et al. | 549/541 |
| 4,243,492 | 1/1981 | Yamamura et al. | 549/542 |

FOREIGN PATENT DOCUMENTS

| | | | |
|---|---|---|---|
| 2108922 | 8/1972 | Fed. Rep. of Germany | 549/542 |
| 47-18811 | 9/1972 | Japan | 549/542 |

Primary Examiner—Norma S. Milestone
Attorney, Agent, or Firm—Jack H. Park; Kenneth R. Priem; Richard A. Morgan

[57] ABSTRACT

Methyl formate is removed from propylene oxide by treatment with a selected base such as sodium hydroxide in water and glycerol. Selected inert salts may be added. The rate of methyl formate hydrolysis by selected bases was increased to commercially acceptable levels by addition of the glycerol. The glycerol and inert salts reduced the amount of residual water in the propylene oxide.

21 Claims, No Drawings

PURIFICATION OF PROPYLENE OXIDE BY TREATMENT WITH A SELECTED BASE AND INERT SALT

CROSS-REFERENCE TO RELATED APPLICATION

This application is related to U.S. patent application Ser. No. 851,842, filed on even date which relates propylene oxide purification with calcium hydroxide in glycerol or sugar water.

BACKGROUND OF THE INVENTION

It is known to prepare propylene oxide by the oxidation of aliphatic hydrocarbons such as propane or butane, or the oxidation of an olefin such as propylene.

In the Oxirane process, propylene oxide is prepared by the catalytic epoxidation of propylene with a hydroperoxide. In the process isobutane is oxidized in the liquid phase without catalyst at 120° to 140° C. and 30 to 35 atm. The resultant liquid is a mixture of reactant hydrocarbons, t-butyl hydroperoxide, t-butyl alcohol, acetone and lesser quantities of other by-products such as ketones, aldehydes, and acids.

Many of the by-products are carried over with the t-butyl hydroperoxide into the second reaction. In the second reaction, propylene is catalytically epoxidized with t-butyl hydroperoxide in liquid phase at high pressure to form propylene oxide. The preferred catalyst is a molybdenum naphthenate organic solution which has a 90 mol percent selectivity on propylene.

The reactions result in complex mixtures containing a number of oxidation products in addition to the propylene oxide. By-products include t-butyl alcohol, ethers, acids, glycols and esters such as methyl formate. Methyl formate has a boiling point near that of propylene oxide, making separation of the two by distillation impractical. In order to obtain propylene oxide suitable for applications, such as the manufacture of polyether polyols used in the preparation of polyurethanes, it is necessary to remove the methyl formate from the propylene oxide.

U.S. Pat. No. 3,477,919 teaches a method for purifying propylene oxide. Propylene oxide prepared by the oxidation of propylene is contaminated with impurities which boil near propylene oxide. The methyl formate impurity is removed from the contaminated propylene oxide by reaction with an aqueous slurry of calcium hydroxide.

U.S. Pat. No. 2,622,060 teaches a process for separating propylene oxide from a crude reaction mixture by treatment with an aqueous alkali metal hydroxide solution.

U.S. Pat. No. 2,550,847 teaches a process for the purification of propylene oxide in a crude reaction mixture containing methyl formate by subjecting the mixture to strong agitation with an aqueous solution of an alkaline saponifying agent.

U.S. Pat. No. 3,350,417 teaches a process for purifying propylene oxide comprising parallel and serial stages of distillation and a caustic treatment to simultaneously aldolize acetaldehyde and saponify methyl formate. The solvent used in the reaction step is removed before subsequent caustic treatment.

U.S. Pat. No. 3,838,020 teaches a process for purifying propylene oxide by extractive distillation with a dual solvent system.

All of these procedures are inherently inefficient in their removal of methyl formate. All of the procedures teach methods of formate removal which suffer from the disadvantage of hydrolysis of propylene oxide to propylene glycol resulting in a depletion of the desired propylene oxide product.

The instant invention is a practical and complete method of removing methyl formate accomplished without significant loss of propylene oxide.

SUMMARY OF THE INVENTION

An improved method has been discovered for removing methyl formate from propylene oxide without appreciable hydrolysis of propylene oxide to propylene glycol. By the method the methyl formate contaminated propylene oxide is contacted with at least a stoichiometric amount of a selected base and glycerol in water. The base is selected from the group consisting of NaOH, KOH, LiOH, $Na_3PO_4$, NaHCO, $NaHCO_3$, $Na_2CO_3$ and $K_2CO_3$. Temperature and pressure conditions are established to produce reaction with the methyl formate. The propylene oxide and glycerol/water separate into different phases. Propylene oxide, substantially free of methyl formate, is recovered by separation.

DESCRIPTION OF THE PREFERRED EMBODIMENTS

The invention is an improvement in U.S. Pat. No. 3,477,919 incorporated herein by reference. The patent teaches the use of a calcium hydroxide slurry to remove the methyl formate contaminant from propylene oxide prepared by the epoxidation of propylene with tertiary butyl hydroperoxide. The boiling points of methyl formate and propylene oxide are very close, making separation of the two by distillation difficult.

U.S. Pat. No. 3,477,919 teaches the use of calcium hydroxide dissolved in aqueous solution to convert the methyl formate to methanol and the calcium salt of formic acid. These reaction products are easily separated from propylene oxide by conventional separation methods. For example, the separation can be effected by a simple distillation using about 40 plates. The method of this patent suffers from a deficiency. That is, the low solubility of calcium hydroxide in water impairs the liquid phase reaction with methyl formate. To partially circumvent this deficiency, the methyl formate is treated with a calcium hydroxide slurry. Slurries are inherently more difficult to work with than a simpler all liquid phase operation.

An improvement has been discovered to calcium hydroxide slurry method. A weak base and glycerol are added to the water. It has been found experimentally that the rate of methyl formate hydrolysis by selected bases can be increased to commercially acceptable levels by the addition of glycerol under mild processing conditions. Surprisingly, the glycerol does not increase the hydrolysis rate of all salts. For example, $NaH_2PO_4$ does not hydrolyze methyl formate. Nor does sodium borate (borax) under mild conditions. Additionally, the presence of glycerol reduces the water content of the propylene oxide layer.

The ratio of crude propylene oxide to water was also found to influence methyl formate hydrolysis rate. Weight ratios of 10/1 to 5/1 were found effective. When weight ratios of 7/1 to 5/1 were used, it was found that reaction rates were increased. This phenomenon is demonstrated in Example 4. This results in improved equipment utilization.

As a general rule, about 10 wt % to about 80 wt % is the most effective working range of the glycerol with 60 wt % to 80 wt % preferred. The concentration of selected base is about 2 to 10 wt % in solution. The glycerol system also forms two phases making a final separation, e.g. distillation, much easier to effect.

The addition of an inert salt to the aqueous base used to hydrolyze methyl formate results in a large drop in water content of the propylene oxide layer and only a small drop in the rate of methyl formate hydrolysis. It was found that an inert salt selected from the group consisting of NaCl, NaBr, HCOONa, KCl, KBr, HCOOK, NaCHO, KCHO, $Na_2SO_4$ and $K_2SO_4$ were effective, in amounts of 5 to 50 wt %. Below about 5 wt % the inert salts showed no beneficial effect. In the cited prior art, these salts were present in concentrations less than 5 wt %. The concentration was ineffective and the beneficial effects heretofore unrecognized. In concentrations above about 50 wt % the inert salts salted out and no additional benefit was realized. These salts dewater propylene oxide reducing the downstream dewatering required.

A preferred base is sodium hydroxide and sodium formate the preferred salt. When sodium hydroxide is used, sodium formate is produced in the hydrolysis reaction. Therefore no make up sodium formate is required once steady state is achieved. Likewise, when lithium hydroxide is the base, the preferred added inert salt is lithium formate.

It is readily apparent from the examples that the system is subject to optimization, with the object being an improved methyl formate hydrolysis. About 2 to 10 wt % selected base in solution is sufficient to hydrolyze methyl formate without catalyzing the reaction of propylene oxide to acetone or propylene glycol. At higher selected base concentrations, contact time is reduced. Temperature is also optimized in the range of 0° C. to 100° C. at atmospheric pressure and above to yield optimum product recovery and equipment utilization.

The invention is distinguished in that the calcium hydroxide slurry is completely eliminated.

This invention is better shown by way of example.

EXAMPLE 1

A 300 cc stainless steel autoclave was charged with 100 ml of a 1% methyl formate, 99% propylene oxide solution. The weak base and water was charged and the autoclave sealed. The mixture was then heated to the desired temperature for the specified time. Stirring was maintained at 600 rpm. At the end of the reaction, the mixture was cooled to ambient temperature and any solids allowed to settle. A small sample was then taken and the products determined by gas chromatograph (GC). The results are reported in Table I. The data in Table I confirms the results of U.S. Pat. No. 3,477,919. Under typical conditions, a $Ca(OH)_2$ or CaO slurry in water is the only suitable base for the removal of methyl formate from PO without forming large quantities of by-product acetone or propylene glycol.

TABLE I

Hydrolysis of Metal Formate in the Presence of Propylene Oxide (a)

| Base | Base grams | $H_2O$ grams | Products: Area % by GC | | | |
|---|---|---|---|---|---|---|
| | | | MeOH | MeF | Acet. | PG |
| $Na_2CO_3$ | 5.00 | 0.31 | 0.080 | 0.956 | 0.438 | 0 |
| $Na_2CO_3$ | 5.00 | 0.61 | 0.079 | 0.971 | 0.416 | 0 |
| CaO | 5.00 | 0.31 | 0.074 | 0.839 | 0.489 | 1.736 |

TABLE I-continued

Hydrolysis of Metal Formate in the Presence of Propylene Oxide (a)

| Base | Base grams | $H_2O$ grams | Products: Area % by GC | | | |
|---|---|---|---|---|---|---|
| | | | MeOH | MeF | Acet. | PG |
| CaO | 5.00 | 0.63 | 0.244 | 0.507 | 0 | 0 |
| $Na_2CO_3$ | 5.00 | 1.54 | 0.082 | 0.927 | 0.951 | 0 |
| CaO | 5.00 | 1.52 | 0.570 | 0 | 0.200 | 0 |
| $NaHCO_3$ | 5.00 | 1.00 | 0.082 | 0.935 | 0.315 | 0 |
| $Li_2CO_3$ | 5.00 | 1.00 | 0.054 | 0.710 | 1.331 | 0.008 |
| $Na_4(PO_4)_2$ | 5.00 | 1.00 | 0.024 | 0.782 | 2.702 | 0.005 |
| $Na_2B_4O_2$ | 5.00 | 1.00 | 0.044 | 0.859 | 0.533 | 0 |
| $La_2O_3$ | 5.00 | 1.00 | 0.045 | 0.562 | 0.406 | 0 |
| CaO | 5.00 | 1.00 | 0.496 | 0 | 0.050 | 0 |
| CaO | 5.00 | 2.00 | 0.485 | 0 | 0.468 | 0.021 |
| CaO | 5.00 | 5.00 | 0.481 | 0 | 0 | 0 |
| $K_2CO_3$ | 5.00 | 2.00 | 0.033 | 0.856 | 0.102 | 0 |
| $Na_2CO_3$ | 5.00 | 2.00 | 0.052 | 0.802 | 0 | 0 |
| ZnO | 5.00 | 2.00 | 0.040 | 0.835 | 0 | 0 |
| Sat. CaO soln. | 3.00 | — | 0.039 | 0.833 | 0 | 0 |
| Sat. CaO soln. | 6.00 | — | 0.043 | 0.793 | 1.067 | 0.050 |
| Sat. CaO soln. | 12.0 | — | 0.056 | 0.740 | 0 | 0.079 |
| 5% $NaHCO_3$ soln. | 5.00 | — | 0.137 | 0.564 | 0 | 0.285 |
| 5% NaOH soln. | 5.00 | — | 0.989 | 0.013 | 0.152 | 30.265 |
| CaO | 1.00 | 5.00 | 0.613 | 0.040 | 0.125 | 0 |
| CaO | 2.00 | 5.00 | 0.462 | 0.008 | 0.162 | 0.029 |
| CaO | 1.00 | 10.0 | 0.410 | 0 | 0.225 | 0.018 |

(a) 60° C., 2 hours
MeOH = methanol; MeF = methyl formate; Acet. = acetone; PG = propylene glycol. Products reported in area % the equivalent of weight %. Water and propylene oxide not reported.

EXAMPLE 2

A 100 ml resin flask equipped with an overhead stirrer (300 rpm), water-cooled condenser, thermometer, and dropping funnel was suspended in a water bath. The temperature was maintained by a resistence heater connected to a Therm-O-Watch ® temperature regulator. The products were determined by GC. Results are shown in Table II.

TABLE II

Hydrolysis of Methyl Formate in a 100 cc Resin Flask[a]

| Base | Base grams | Time (min) | Temp[b] (°C.) | % MeF Hydrolysis | % $H_2O$ |
|---|---|---|---|---|---|
| 6% NaOH in 70% Glycerol | 13.0 | 60 | 15 | 100 | 2.06 |
| 5% Aqueous NaOH | 11.1 | 60 | 16 | 100 | 8.51 |
| 20% Aqueous Na Formate | 9.0 | 45 | 21 | 0 | — |
| 20% Aqueous Na Formate | 9.0 | 60 | 30 | 5.0 | 7.29 |
| 6% Na Formate in 70% Glycerol | 12.6 | 60 | 30 | 13.7 | 2.41 |
| 3% $NaHCO_3$ in 70% Glycerol | 11.6 | 60 | 30 | 38.1 | 3.15 |
| 6% $K_2CO_3$ in 70% Glycerol | 10.7 | 60 | 30 | 64.6 | 2.52 |
| 6% $K_2CO_3$ in 70% Glycerol | 21.1 | 60 | 30 | 84.5 | 2.95 |
| 6% Aqueous $K_2CO_3$ | 11.5 | 60 | 30 | 39.2 | 11.62 |
| 6% $NaH_2PO_4$ in 70% Glycerol | 11.1 | 60 | 30 | 0 | 2.95 |
| 6% $Na_3PO_4$ in 70% Glycerol | 11.9 | 60 | 30 | 39.8 | 2.74 |
| 6% Borax in 70% Glycerol | 13.4 | 60 | 30 | 0 | 3.78 |

[a] 50.0 g of 1% methyl formate in propylene oxide Stirring speed = 300 rpm
[b] Temperature +/− 1° C.

EXAMPLE 3

A. 11.1 g 5% aqueous NaOH was added to 50.0 g of 1% methyl formate in propylene oxide. The mixture was stirred at 300 rpm and 16° C. +/−1° C. in a 100 ml resin flask equipped with overhead stirrer and water-cooled condenser. Aliquots were withdrawn at the times indicated and analyzed by GC and reported in area %.

| Time | Products by GC area % | | | |
|---|---|---|---|---|
| (min) | MeOH | MeF | Unk. | PG |
| 0 | trace | 0.963 | 0 | 0 |
| 2 | 0.370 | 0 | 0.048 | 0.005 |
| 6 | 0.385 | 0 | 0 | 0.009 |
| 10 | 0.383 | 0 | 0.011 | 0.011 |
| 20 | 0.368 | 0 | 0.008 | 0.011 |
| 45 | 0.371 | 0.003 | 0.016 | 0.044 |
| 60 | 0.371 | 0 | 0.004 | 0.061 |

The average water content in the propylene oxide layer was 9.23%.

B. The procedure was the same as A, except that 11.8 g of 4.75% NaOH/5.0% NaCl in water was reacted with 50.0 g, 1% methyl formate in propylene oxide at 30° C.+/−1° C.

| Time | Products by GC area % | | | |
|---|---|---|---|---|
| (min) | MeOH | MeF | Unk. | PG |
| 0 | trace | 0.963 | 0 | 0 |
| 3 | 0.520 | 0 | 0.187 | 0 |
| 6 | 0.427 | 0 | 0.014 | 0 |
| 12 | 0.410 | 0 | 0.023 | 0 |
| 24 | 0.401 | 0 | 0.030 | 0 |
| 50 | 0.406 | 0 | 0.089 | 0.235 |
| 120 | 0.417 | 0 | 0.160 | 0.235 |

C. 30.0 ml, 1% methyl formate in PO was extracted three times with 5.0 ml 4.75% NaOH/5% NaCl in a small separatory funnel at ambient temperature (20° C.). A small aliquot was withdrawn after each extraction and the products determined by GC.

| | Products by GC area % | | | |
|---|---|---|---|---|
| | MeOH | MeF | Unk. | PG |
| initial | 0.016 | 0.984 | 0.032 | 0 |
| after 1st extraction | 0.401 | 0 | 0.044 | 0 |
| after 2nd extraction | 0.274 | 0 | 0.010 | 0.009 |
| after 3rd extraction | 0.181 | 0 | 0.007 | 0 |

The average percent water in the propylene oxide layer was 9.51%.

D. The procedure was the same as C, except that 5% NaOH/10% NaCl was used as the extractant.

| | Products by GC area % | | | |
|---|---|---|---|---|
| | MeOH | MeF | Unk. | PG |
| initial | 0.016 | 0.984 | 0.032 | 0 |
| after 1st extraction | 0.365 | 0 | 0.011 | 0 |
| after 2nd extraction | 0.283 | 0 | 0 | 0 |
| after 3rd extraction | 0.210 | 0 | 0.016 | 0 |

The average percent water was 8.11%, a small but significant drop in the percent water present in the propylene oxide.

E. The procedure was the same as C, except that 5% NaOH/20% NaCl was used as the extractant.

| | Products by GC area % | | | |
|---|---|---|---|---|
| | MeOH | MeF | Unk. | PG |
| initial | 0.016 | 0.984 | 0.032 | 0 |
| after 1st extraction | 0.251 | 0.441 | 0.003 | 0 |
| after 2nd extraction | 0.337 | 0 | 0.0001 | 0 |
| after 3rd extraction | 0.236 | 0 | 0 | 0 |

The average percent water present in the propylene oxide layer was 4.85%, a significant drop over no added salt.

F. The procedure was the same as C, except that 5% NaOH/30% sodium formate was used as the extractant.

| | Products by GC area % | | | |
|---|---|---|---|---|
| | MeOH | MeF | Unk. | PG |
| initial | 0.016 | 0.984 | 0 | 0 |
| after 1st extraction | 0.402 | 0.072 | 0.001 | 0 |
| after 2nd extraction | 0.346 | 0.002 | 0 | 0 |
| after 3rd extraction | 0.250 | 0 | 0 | 0 |

The average percent water present in the propylene oxide layer was 4.40%, a significant drop when compared to the experiment in which no salt was added.

G. The procedure was the same as C, except that 5% NaOH/40% sodium formate was used as the extractant.

| | Products by GC area % | | | |
|---|---|---|---|---|
| | MeOH | MeF | Unk. | PG |
| initial | 0.016 | 0.984 | 0 | 0 |
| after 1st extraction | 0.294 | 0.332 | 0.003 | 0 |
| after 2nd extraction | 0.311 | 0.063 | 0 | 0 |
| after 3rd extraction | 0.279 | 0.008 | 0 | 0 |

The average percent water present in the propylene oxide layer was 2.90%.

H. The procedure was the same as that described in A, except that 11.0 g, 5% NaOH/40% sodium formate was added to the reactor. (Temp. 20° C. +/−1° C.).

| Time | Products by GC area % | | | |
|---|---|---|---|---|
| (min) | MeOH | MeF | Unk. | PG |
| 0 | trace | 0.969 | trace | 0 |
| 2 | 0.136 | 0.781 | trace | 0 |
| 5 | 0.266 | 0.584 | trace | 0 |
| 9 | 0.403 | 0.382 | trace | 0 |
| 16 | 0.528 | 0.191 | trace | 0 |
| 30 | 0.623 | 0.054 | trace | 0 |
| 60 | 0.628 | 0 | trace | 0.033 |

The percent water present in H. was 2.80%, a large drop in the percent water present in the propylene oxide when compared to the control experiment A.

EXAMPLE 4

A. A 100 ml resin flask equipped with an overhead stirrer, thermometer, and water cooled condenser was charged with 50.0 g methyl formate in propylene oxide. The mixture was stirred at 300 rpm and the temperature maintained by means of a resistance heater suspended in a small water bath. Calcium hydroxide (0.42 g) was charged along with 10.0 g water. Aliquots were withdrawn at the time indicated and analyzed by GC. The results are reported here.

| Time (min) | Temp. (°C.) | MeOH Wt. % | MeF Wt. % | $H_2O$ Wt. % | PO Wt. % |
|---|---|---|---|---|---|
| 0 | 30.2 | trace | 0.879 | — | — |
| 2 | 30.5 | 0.191 | 0.516 | — | — |
| 5 | 31.0 | 0.361 | 0.053 | — | — |
| 10 | 30.0 | 0.353 | ~0 | — | — |
| 16 | 29.8 | 0.432 | ~0 | — | — |
| 30 | 29.8 | 0.474 | ~0 | 14.47 | 85.18 |
| (lower layer) | | 0.619 | ~0 | 79.76 | 19.35 |

B. The procedure was the same as A, except that 5.0 g water was charged.

| Time (min) | Temp. (°C.) | MeOH Wt. % | MeF Wt. % | $H_2O$ Wt. % | PO Wt. % |
|---|---|---|---|---|---|
| 0 | 30.0 | trace | 0.881 | — | — |
| 2 | 29.9 | 0.068 | 0.782 | — | — |
| 5 | 30.5 | 0.112 | 0.702 | — | — |
| 10 | 29.9 | 0.115 | 0.681 | — | — |
| 30 | 30.2 | 0.214 | 0.588 | — | — |
| 60 | 30.1 | 0.248 | 0.499 | 12.40 | 86.95 |

C. The procedure was the same as A, except that 7.0 g water was used.

| Time (min) | Temp. (°C.) | MeOH Wt. % | MeF Wt. % | $H_2O$ Wt. % | PO Wt. % |
|---|---|---|---|---|---|
| 0 | 29.2 | trace | 0.877 | — | — |
| 2 | 29.8 | 0.080 | 0.747 | — | — |
| 6 | 30.8 | 0.316 | 0.368 | — | — |
| 12 | 29.8 | 0.340 | 0.294 | — | — |
| 18 | 30.0 | 0.437 | 0.226 | — | — |
| 30 | 30.0 | 0.445 | 0.143 | — | — |
| 60 | 30.1 | 0.440 | 0.025 | 14.76 | 84.77 |

D. The procedure was the same as A except that 8.0 g water was charged.

| Time (min) | Temp. (°C.) | MeOH Wt. % | MeF Wt. % | $H_2O$ Wt. % | PO Wt. % |
|---|---|---|---|---|---|
| 0 | 30.0 | trace | 0.877 | — | — |
| 2 | 29.5 | 0.193 | 0.526 | — | — |
| 4 | 30.0 | 0.383 | 0.196 | — | — |
| 9 | 29.0 | 0.388 | 0.091 | — | — |
| 16 | 29.1 | 0.463 | 0.031 | — | — |
| 30 | 29.6 | 0.522 | 0.003 | 14.71 | 84.84 |

E. The procedure was the same as A, except that 6.0 g water was charged.

| Time (min) | Temp. (°C.) | MeOH Wt. % | MeF Wt. % | $H_2O$ Wt. % | PO Wt. % |
|---|---|---|---|---|---|
| 0 | 28.2 | trace | 0.870 | — | — |
| 2 | 29.5 | 0.051 | 0.811 | — | — |
| 6 | 30.3 | 0.098 | 0.701 | — | — |
| 15 | 29.5 | 0.123 | 0.678 | — | — |
| 30 | 29.7 | 0.159 | 0.612 | — | — |
| 60 | 30.0 | 0.226 | 0.535 | 12.62 | 86.68 |

F. The procedure was the same as A, except that 6.5 g water was used.

| Time (min) | Temp. (°C.) | MeOH Wt. % | MeF Wt. % | $H_2O$ Wt. % | PO Wt. % |
|---|---|---|---|---|---|
| 0 | 28.0 | trace | 0.877 | — | — |
| 2 | 29.4 | 0.071 | 0.788 | — | — |
| 5 | 30.6 | 0.181 | 0.573 | — | — |
| 12 | 30.1 | 0.240 | 0.478 | — | — |
| 18 | 29.8 | 0.243 | 0.463 | — | — |
| 30 | 29.9 | 0.254 | 0.416 | — | — |
| 60 | 30.0 | 0.378 | 0.296 | 13.37 | 85.96 |

G. The procedure was the same as A, except that 8.0 g water was used and the stirring speed was 600 rpm.

| Time (min) | Temp. (°C.) | MeOH Wt. % | MeF Wt. % | $H_2O$ Wt. % | PO Wt. % |
|---|---|---|---|---|---|
| 0 | 28.2 | trace | 0.879 | — | — |
| 2 | 29.1 | 0.191 | 0.670 | — | — |
| 6 | 30.3 | 0.495 | 0.119 | — | — |
| 12 | 30.0 | 0.471 | 0.045 | — | — |
| 30 | 30.0 | 0.569 | ~0 | 13.30 | 86.25 |

H. The procedure was the same as that described in A, except that 8.0 g water was used and the stirring rate was 200 rpm.

| Time (min) | Temp. (°C.) | MeOH Wt. % | MeF Wt. % | $H_2O$ Wt. % | PO Wt. % |
|---|---|---|---|---|---|
| 0 | 27.8 | trace | 0.870 | — | — |
| 2 | 28.6 | 0.149 | 0.659 | — | — |
| 6 | 30.3 | 0.481 | 0.152 | — | — |
| 10 | 29.7 | 0.538 | 0.096 | — | — |
| 15 | 30.0 | 0.478 | 0.062 | — | — |
| 30 | 29.8 | 0.477 | 0.011 | 14.22 | 85.32 |

I. The procedure was the same as A, except that 8.0 g water and 0.296 g calcium hydroxide were used.

| Time (min) | Temp. (°C.) | MeOH Wt. % | MeF Wt. % | $H_2O$ Wt. % | PO Wt. % |
|---|---|---|---|---|---|
| 0 | 28.0 | trace | 0.867 | — | — |
| 2 | 29.2 | 0.143 | 0.616 | — | — |
| 5 | 30.9 | 0.387 | 0.179 | — | — |
| 10 | 30.2 | 0.422 | trace | — | — |
| 15 | 30.0 | 0.649 | trace | — | — |
| 30 | 29.8 | 0.587 | ~0 | 14.81 | 84.68 |

J. The procedure was the same as A, except that 8.0 g water was used and the temperature was maintained at 21° C. +/−1° C.

| Time (min) | Temp. (°C.) | MeOH Wt. % | MeF Wt. % | $H_2O$ Wt. % | PO Wt. % |
|---|---|---|---|---|---|
| 0 | 19.5 | 0.007 | 0.850 | — | — |
| 2 | 20.0 | 0.087 | 0.721 | — | — |
| 5 | 21.0 | 0.223 | 0.430 | — | — |
| 10 | 21.2 | 0.402 | 0.090 | — | — |
| 16 | 21.0 | 0.488 | 0.041 | — | — |
| 22 | 21.1 | 0.458 | 0.024 | — | — |

-continued

| Time (min) | Temp. (°C.) | MeOH Wt. % | MeF Wt. % | H₂O Wt. % | PO Wt. % |
|---|---|---|---|---|---|
| 45 | 21.0 | 0.049 | ~0 | 12.47 | 87.12 |

K. The procedure was the same as that described in A, except that 8.0 g water was used and the temperature was maintained at 1° C. +/−1° C.

| Time (min) | Temp. (°C.) | MeOH Wt. % | MeF Wt. % | H₂O Wt. % | PO Wt. % |
|---|---|---|---|---|---|
| 0 | 1.0 | 0.008 | 0.848 | — | — |
| 2 | 1.0 | 0.040 | 0.807 | — | — |
| 5 | 0.9 | 0.069 | 0.745 | — | — |
| 15 | 1.2 | 0.211 | 0.461 | — | — |
| 21 | 0.4 | 0.312 | 0.313 | — | — |
| 30 | 0.1 | 0.365 | 0.158 | — | — |
| 45 | 1.7 | 0.389 | 0.064 | — | — |
| 62 | 1.2 | 0.390 | 0.033 | 11.07 | 88.50 |

L. The procedure was the same as A, except that 8.0 g water was used and the temperature was maintained at 10° C. +/−1° C.

| Time (min) | Temp. (°C.) | MeOH Wt. % | MeF Wt. % | H₂O Wt. % | PO Wt. % |
|---|---|---|---|---|---|
| 0 | 8.5 | trace | 0.855 | — | — |
| 2 | 8.9 | 0.052 | 0.772 | — | — |
| 5 | 9.2 | 0.145 | 0.609 | — | — |
| 10 | 10.0 | 0.234 | 0.366 | — | — |
| 15 | 10.0 | 0.344 | 0.170 | — | — |
| 22 | 9.7 | 0.449 | 0.055 | — | — |
| 33 | 10.0 | 0.434 | ~0.01 | — | — |
| 45 | 10.0 | 0.458 | ~0 | 11.89 | 87.71 |

Many modifications may be made to the method of this invention without departing from the spirit and scope of the invention which is defined only in the appended claims. For example, one skilled in the art could adjust the temperature, pressure, proportions and modes of contacting, either batch, semi-batch or continuous to provide propylene oxide free of the methyl formate contaminant.

What is claimed is:

1. A method for removing methyl formate from propylene oxide which comprises:
    contacting propylene oxide containing methyl formate with a base selected from the group consisting of NaOH, KOH, LiOH, Na₃PO₄, NaHCO, NaHCO₃, Na₂CO₃ and K₂CO₃ in an amount at least stoichiometrically equivalent to the methyl formate and glycerol in water,
    establishing temperature and pressure conditions which produce a reaction between methyl formate and the weak base and
    separating and recovering propylene oxide substantially free of methyl formate.
2. The method of claim 1 wherein the base is in an amount about 1.25 times the stoichiometric equivalent of methyl formate present.
3. The method of claim 1 wherein the glycerol is present in an amount of 10 to 80 wt %.
4. The method of claim 1 wherein the glycerol is present in an amount of 60 to 80 wt %.
5. The method of claim 1 wherein the base is Na₃PO₄.
6. The method of claim 1 wherein the base is NaHCO.
7. The method of claim 1 wherein the base is NaOH.
8. The method of claim 1 wherein the weight ratio of propylene oxide to water is about 10/1 to 5/1.
9. The method of claim 1 wherein the weight ratio of propylene oxide to water is about 7/1 to 5/1.
10. A method for removing methyl formate from propylene oxide which comprises:
    contacting propylene oxide containing methyl formate with a base selected from the group consisting of NaOH, KOH, LiOH, Na₃PO₄, Na₂CO₃ and K₂CO₃ in an amount at least stoichiometrically equivalent to the methyl formate; and a propylene oxide dehydrating amount of an inert salt selected from the group consisting of NaCl, NaBr, HCOONa, KCl, KBr, HCOOK, NaCHO, KCHO, Na₂SO₄ and K₂SO₄ in water,
    establishing temperature and pressure conditions which produce a reaction between methyl formate and the weak base and
    separating and recovering propylene oxide substantially free of methyl formate.
11. The method of claim 10 wherein the base is in an amount about 1.25 times the stoichiometric equivalent of methyl formate present.
12. The method of claim 10 wherein the base is NaOH.
13. The method of claim 10 wherein the weight ratio of propylene oxide to water is about 10/1 to 5/1.
14. The method of claim 10 wherein the weight ratio of propylene oxide to water is about 7/1 to 5/1.
15. The method of claim 10 wherein the inert salt is NaCl.
16. The method of claim 10 wherein the inert salt is NaOOCH.
17. The method of claim 10 wherein the inert salt is present in an amount of 5 to 50 wt %.
18. The method of claim 10 wherein the base is sodium hydroxide and the inert salt is sodium formate.
19. The method of claim 10 wherein the base is lithium hydroxide and the inert salt is lithium formate.
20. The method of claim 10 wherein the base is selected from the group consisting of sodium hydroxide, potassium hydroxide and lithium hydroxide.
21. The method of claim 10 wherein glycerol is present with the water.

* * * * *